US008722060B2

(12) United States Patent
Binder

(10) Patent No.: US 8,722,060 B2
(45) Date of Patent: May 13, 2014

(54) METHOD OF TREATING VERTIGO

(76) Inventor: William J. Binder, Beverly Hills, CA (US)

( * ) Notice: Subject to any disclaimer, the term of this patent is extended or adjusted under 35 U.S.C. 154(b) by 0 days.

(21) Appl. No.: 13/478,640

(22) Filed: May 23, 2012

(65) Prior Publication Data

US 2013/0315957 A1 Nov. 28, 2013

(51) Int. Cl.
*A61K 39/08* (2006.01)
(52) U.S. Cl.
USPC .................. 424/239.1; 424/247.1; 424/234.1; 424/236.1
(58) Field of Classification Search
None
See application file for complete search history.

(56) References Cited

U.S. PATENT DOCUMENTS

| | | | | |
|---|---|---|---|---|
| 6,265,379 | B1 * | 7/2001 | Donovan | 514/18.1 |
| 6,358,926 | B2 * | 3/2002 | Donovan | 424/780 |
| 6,806,251 | B2 * | 10/2004 | Lamb | 424/780 |
| 7,270,287 | B2 * | 9/2007 | First | 424/239.1 |
| 7,491,403 | B2 * | 2/2009 | Borodic | 424/239.1 |
| 2001/0025024 | A1 * | 9/2001 | Donovan | 514/2 |
| 2004/0204471 | A1 * | 10/2004 | Seibert | 514/406 |
| 2004/0247606 | A1 * | 12/2004 | Borodic et al. | 424/184.1 |
| 2005/0106183 | A1 * | 5/2005 | Lamb | 424/239.1 |
| 2005/0147625 | A1 * | 7/2005 | First | 424/239.1 |
| 2006/0276510 | A1 * | 12/2006 | Abu-Shakra et al. | 514/332 |
| 2008/0003242 | A1 * | 1/2008 | First | 424/239.1 |

* cited by examiner

*Primary Examiner* — Albert Navarro
*Assistant Examiner* — Ginny Portner

(57) ABSTRACT

The invention is a method for reducing the symptoms of vertigo. The method is performed by delivering a therapeutically effective amount of presynaptic neurotoxin, such as Botulinum Toxin A, in a pharmaceutically safe form to suitable locations around the head and neck.

5 Claims, No Drawings

METHOD OF TREATING VERTIGO

BACKGROUND OF THE INVENTION

Vertigo is the feeling that you or your environment is moving or spinning. It differs from dizziness in that vertigo describes an illusion of movement where there is a feeling of movement when one is stationary. When you feel as if you yourself are moving, it's called subjective vertigo, and the perception that your surroundings are moving is called objective vertigo. Vertigo is thought to be caused by problems in the brain or in the inner ear.

With vertigo there is a sensation of motion either of the person or the environment, often perceived as if the room is spinning around you. This should not be confused with symptoms of lightheadedness or fainting. Vertigo differs from motion sickness in that motion sickness is a feeling of being off-balance and lacking equilibrium, caused by repeated motions such as riding in a car or boat. Symptoms include a sensation of disorientation or motion. In addition, the individual may also have one or more of the following symptoms; nausea or vomiting, sweating and/or abnormal eye movements.

The duration of symptoms can be from minutes to hours, and symptoms can be constant or episodic. The onset may be due to a movement or change in position, head trauma or whiplash injury as well as any new medications the affected individual is taking. A person may have hearing loss and a ringing sensation in the ears or visual disturbances, weakness, difficulty speaking, a decreased level of consciousness, and difficulty walking.

Vertigo may be caused by a number of internal or external factors. For example, the most common form of vertigo is benign paroxysmal positional vertigo (BPPV, characterized by the sensation of motion initiated by sudden head movements or moving the head in a certain direction.

Vertigo may also be caused by inflammation within the inner ear (labyrinthitis or vestibular neuritis), which is characterized by the sudden onset of vertigo and may be associated with hearing loss. The most common cause of labyrinthitis is a viral or bacterial inner ear infection. Otoliths (stones) in the ear canals can also cause vertigo.

Meniere's disease is a disorder of the inner ear composed of a triad of symptoms including: episodes of vertigo, ringing in the ears (tinnitus), and hearing loss. People with this condition have an abrupt onset of severe vertigo, fluctuating hearing loss, as well as periods in which they are symptom-free.

Vertigo is often the presenting symptom in multiple sclerosis. The onset is usually abrupt, and examination of the eyes may reveal the inability of the eyes to move past the midline toward the nose. Head trauma, neck injury and concussions may also result in vertigo.

Migraine-associated vertigo (MAV) or vertiginous migraine is a recognized disease condition consisting of dizziness and/or vertigo. Other terms used to describe this condition include vestibular migraine, migrainous vertigo, or migraine-related vestibulopathy. While thought to be related to migraine headache, patients diagnosed with MAV and the like do not have classic migraine headaches, or have chronic non-specific headaches that do not fit into the migraine classification developed by the International Headache Society.

Persons with MAV often describe chronic dizziness and disequilibrium in the form of a "rocking" sensation. Sometimes the vertiginous effects are described as episodes of rotational vertigo, changes in vision, visual "snow", nausea and severe motion intolerance. Neurological examinations (including neuroimaging) are often completely normal. Patients with chronic dizziness often do not experience acute rotational vertigo or even the pain of a migraine headache.

Commonly prescribed medications for vertigo include meclizine hydrochloride (Antivert), diphenhydramine (Benadryl), scopolamine transdermal patch (Transderm-Scop) and promethazine hydrochloride (Phenergan).

SUMMARY OF THE INVENTION

The invention relates to a method of reducing the symptoms of vertigo comprising administering to a human having vertigo a therapeutically effective amount of a presynaptic neurotoxin in a pharmaceutically safe form. Typical forms of the presynaptic neurotoxin that may be used in the invention include Botulinum toxins type A, B, C, D, E, F and G and preferably Botulinum toxin A and more preferably onabotulinumtoxinA. In addition, an Endotoxin may be used, such as an Endotoxin derived from Botulinum toxin. The vertigo to be treated may be any of the many forms of vertigo disclosed herein.

DETAILED DESCRIPTION OF THE INVENTION

Some patients are very sensitive to motion of the environment and to busy environments.

Vertigo, which is an illusion of movement of the environment or of the patient in relation to the environment, is the most common type of dizziness reported, and it is present at some time in approximately 70% of patients. The attacks of vertigo may awaken patients and are usually spontaneous, but they may be provoked by motion. The duration of the vertigo can also be quite variable from only seconds to over 24 hours and recurrent or episodic vertigo attacks may last for up to weeks or even months.

"Presynaptic neurotoxin" as used herein refers to both invertebrate toxins and biologically active peptide fragments of proteinaceous invertebrate toxins. The preferred presynaptic neurotoxin is Botulinum toxin, serotype A. The preferred form of Botulinum toxin A is onabotulinumtoxinA, which is commercially available. Other Botulinum toxins may also be used including Botulinum toxins B, C, D, E, F or G.

Preferably the presynaptic neurotoxins of the invention will be administered as a composition in a pharmaceutically acceptable carrier such as saline solution. For example, a typical dilution is from 1-10 cc saline per 100 units of onabotulinumtoxinA depending on the amount and place of injection. Preferably, a presynaptic neurotoxin, such as onabotulinumtoxinA, will be administered as a composition at a dosage that is equivalent to about 2-8 cc/100 units or more preferably 2 cc/100 units. Those of ordinary skill in the art can ascertain how to adjust these dosages for presynaptic neurotoxins of greater or lesser potency.

The preferred target site for injection of the presynaptic neurotoxin will be in or near the muscle and/or extramuscular regions of the face cranium and neck. The most preferred sites are the bilateral, temporal, frontal, glabella and suboccipital areas of the face and head as well as specific target areas of the neck and shoulders. The corrugator, procerus, temporal and fromtalis muscles are also suitable sites for introduction of the presynaptic neurotoxins. A typical treatment amount varies from about 50 to 250 units, but may be more or less depending on the patient and his condition and the potency of the neurotoxin used in treatment. A typical treatment amount of onabotulinumtoxinA is about 150 units.

EXAMPLES

Case 1

MAV

A 54 year old man presented with a long history of vertigo. The onset of vertigo began with minor episodes while the patient was in college. It then presented acutely with an incapacitating episode. The following year, the vertigo then recurred periodically. The patient then had an episode that lasted for 1 month with both symptoms of spinning and imbalance. The patient was worked up diagnostically by ear specialists, otologists, neurologists. Allergy testing was negative. Numerous CT and MRI scans and inner ear testing all proved to be normal with no evidence of tumors or vascular lesions. The diagnosis was confirmed by numerous specialists to be migraine associated vertigo or that of possible vascular origin. Treatment included various antihistamines such as diphenhydramine, meclizine hydrochloride, and scopolamine which did not control the symptoms of vertigo.

During the past 12 months, prior to initial consultation, the vertigo at times became incapacitating whereby the patient became confined to bed for periods of 24-48 hours. Over the last most 6 months, the patient experienced a frequency of two episodes of vertigo per month, each lasting 2-3 days, and then leaving the patient with prolonged periods of residual imbalance. The patient was recently treated with a trial of high dose Prednisone without success.

The initial treatment consisted of using OnabotulinumtoxinA with a dilution of 4 cc per 100 units. Each injection comprised between 0.1 cc (2.5 units) and 0.2 cc (5 units) which was applied to multiple sites over the glabella, forehead, temporal, occipital and suboccipital areas of the head and neck. In addition, the injections were applied to areas of the neck including the trapezius muscle. The number of units used in the initial treatment totaled approximately 150 units of OnabotulinumtoxinA. The patient was seen 3 months later and reported that the symptoms of vertigo were completely eliminated. The patient was then treated at consecutive periods of 3 month intervals with varying does between 150-175 units of OnabotulinumtoxinA. The vertigo was consistently eliminated with each treatment. The patient reported only one episode when the treatment period was extended beyond 4 months. The patient has continued OnabotulinumtoxinA injections as a preventive therapy for the vertigo.

Case 2

A 58 year old woman with chronic disabling vertigo presents for assessment and treatment. She has been diagnosed with otoliths in her semi-circular canals and any change in head position triggers vertigo. If she rolls over in bed, she awakens with severe vertigo. She has tried oral medications such as meclizine without benefit. She was treated with centrifugal force from an Otolaryngologist without change. Her brain MRI scans have all been normal.

She is treated with OnabotulinumtoxinA: 2 cc dilution per 100 units. Injections given as follows: 0.1 cc (5 units) injections in 5 sites in each temporalis muscle and area and 0.1 cc (5 units) in 5 sites in each occipitalis muscle and area. The procedure is well tolerated without side effects. Six weeks later she notes a progressive improvement in her vertigo. Initially greater stimuli are required to bring on the symptoms. At 12 weeks, she has her second OnabotulinumtoxinA treatment with the same sites and dosing. After this, she develops progressively more vertigo free days. As a result, she is able to return to work as a cashier.

What is claimed is:

1. The method for treating Migraine Associated Vertigo comprising administering to a human having Migraine Associated Vertigo a therapeutically effective amount of a presynaptic neurotoxin in a pharmaceutically safe form.

2. The method according to claim 1 wherein the presynaptic neurotoxin is a Botulinum toxin.

3. The method according to claim 2 wherein the Botulinum toxin is Botulinum toxin A.

4. The method according to claim 2 wherein the Botulinum toxin is Botulinum toxin B.

5. The method according to claim 3 wherein the botulinum toxin A is onabotulinumtoxinA.

\* \* \* \* \*